United States Patent [19]

Kyotani

[11] Patent Number: 4,834,655
[45] Date of Patent: May 30, 1989

[54] CUTTING TOOLS
[75] Inventor: Ikuo Kyotani, Kitamoto, Japan
[73] Assignee: G-C Dental Industrial Corp., Tokyo, Japan
[21] Appl. No.: 38,900
[22] Filed: Apr. 16, 1987
[30] Foreign Application Priority Data Jun. 4, 1986 [JP] Japan .................................. 61-128079
Nov. 28, 1986 [JP] Japan .................................. 61-281993

[51] Int. Cl.⁴ ............................................... A61C 3/06
[52] U.S. Cl. .................................... 433/166; 51/206 P
[58] Field of Search ............. 433/165, 166; 51/206 R, 51/206 P; 408/145

[56] References Cited

U.S. PATENT DOCUMENTS

| | | | |
|---|---|---|---|
| 1,961,891 | 6/1934 | Miller | 51/206 P |
| 2,178,491 | 10/1939 | Palotce | 51/206 P |
| 3,309,772 | 3/1967 | Lieb et al. | 433/166 |
| 3,462,887 | 8/1969 | Hackman, Jr. | 51/206 P |
| 4,083,351 | 4/1978 | Greenspan | 125/30 R |
| 4,466,795 | 8/1984 | Plischka | 433/166 |
| 4,635,407 | 1/1987 | Pacini | 51/206 R |
| 4,661,064 | 4/1987 | Beltramini | 433/166 |

FOREIGN PATENT DOCUMENTS 732124 6/1955 United Kingdom ................ 433/165

Primary Examiner—Samuel Scott
Assistant Examiner—Allen J. Flanigan
Attorney, Agent, or Firm—Oblon, Fisher, Spivak, McClelland & Maier

[57] ABSTRACT

A cutting tool include a shank having a head, a groove which is formed on the outer face portion of the head only in the dextrally spiral form, and hard abrasive grains-attached section formed on the outer face portion of the head except for the groove. The total sum of the width of the groove in the section normal to the axis of the head of the shank is in a range of (1/50 to 2/5)×πD, except for the endmost terminating portion of the head, wherein D is the diameter of the section normal to the axis of the head.

1 Claim, 3 Drawing Sheets

FIG. 3
FIG. 4
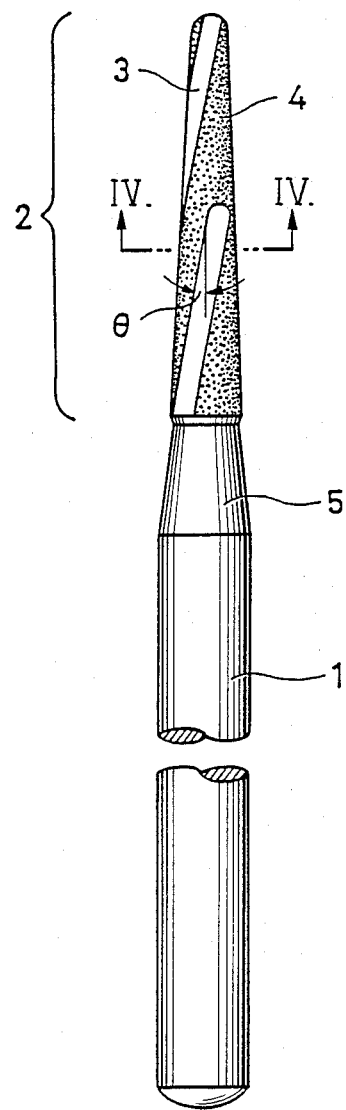
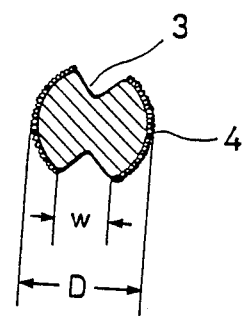

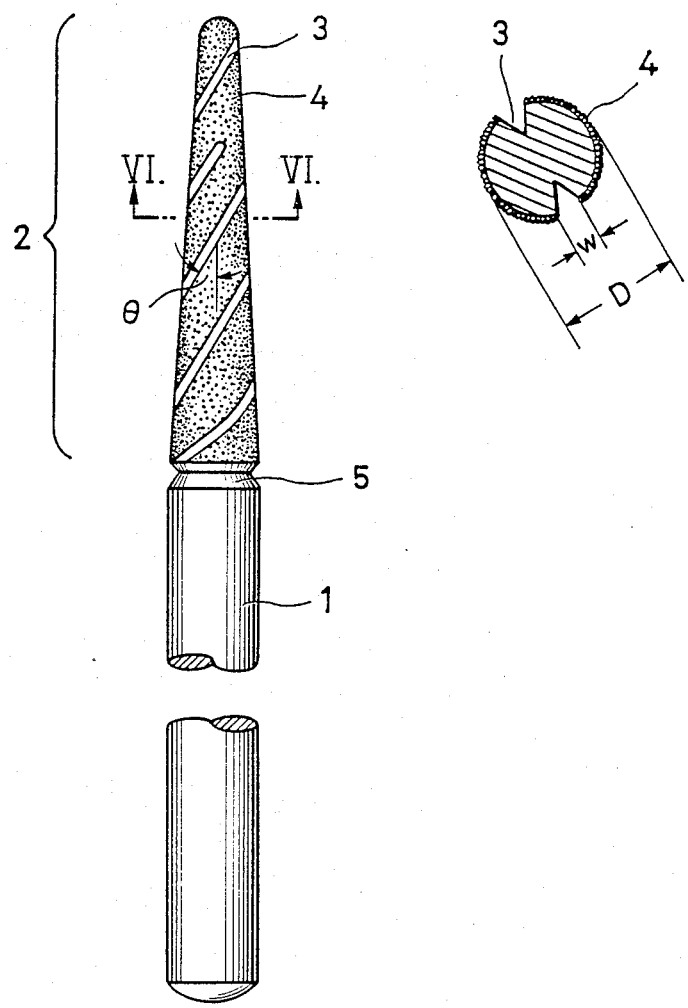

CUTTING TOOLS

BACKGROUND OF THE INVENTION

1. Field of the Invention

The present invention relates to a cutting tool and, more particularly, to a dental rotary instrument which is adapted to be used for cutting teeth or dental restorations, and is also designed to be used for cutting other materials.

2. Statement of the Prior Art

In general, dental rotary instruments are made by attaching hard abrasive grains such as those based on natural or artificial diamond, aluminum oxide or carborundum on a shank molded or otherwise formed into various shapes such as spherical, cylindrical, conical, wheel shapes and others by means of electroplating or brazing. For use, the dental rotary instruments are mounted on a dental turbine or a dental engine, and they are rotated at a high speed while cooled with poured water or sprayed water at the same time.

For dentists, it is preferred to carry out efficient preparation with such dental rotary instruments, and this is also desirable for patients. Required for that purpose are that:

(1) the cutting tools used excel in cutting efficiency,
(2) the removal of debris produced by cutting teeth or dental restorations is satisfactorily effected, and
(3) the removal of heat generated at teeth or dental restorations and the head of the cutting tool in association with preparation is satisfactorily effected.

Now, various dental rotary instruments to meet such requirements have been proposed.

According to one typical example, three spiral grooves are formed on the outer face portion of the head of a shank, which are formed slightly dextrally with respect to the axis of the head. According to another example disclosed in Japanese patent laid-open publication No. 56-31744, a stack of symmetrical beads of Japanese soroban, each of a hexagonal shape in cross-section, is grooved. According to still another example disclosed in Japanese patent laid-open publication No. 58-500280, a groove having a lefthand thread is provided.

Each of the cutting tools as mentioned above poses the following problems.

The first-mentioned example of cutting tools shows excellent cutting efficiency, when the head of its shank has a large outer diameter. If the head has a small outer diameter, however, the area ratio of the hard abrasive grains-attached section in the head of the shank of the cutting tool is so reduced due to the presence of three grooves that the area of contact of that section with teeth or dental restorations is reduced, thus leading to a lowering of cutting efficiency. This tendency become more marked when a low load is applied.

Referring to the second-mentioned example of cutting tools, the area of the hard abrasive grains-attached section to contact flat teeth or dental restorations during preparation is greatly reduced, leading to a lowering of cutting efficiency. In addition, since the portion of the head is machined in the form of a groove, it is required to readjust the thus grooved portion with the use of an ordinary cutting tool which is not grooved.

The third-mentioned example of cutting tools has the disadvantage that, due to the fact that the width of the groove is virtually equal to the width of the hard abrasive grains-attached section, the area of the hard abrasive grains-attached section to contact teeth or dental restorations is decreased to about ½ of the area of the head, with the result that the cutting efficiency drops at the same revolutions per minute.

OBJECT OF THE INVENTION

A main object of the present invention is to provide a dental rotary instrument which excels in cutting efficiency and, at the same time, makes satisfactory removal of debris and heat.

SUMMARY OF THE INVENTION

According to the present invention, the foregoing object is achieved by the provision of a cutting tool including a shank having head with a groove which is formed on the outer face portion of said head in the dextrally spiral form alone, and a hard abrasive grains-attached section formed on the head except for the groove, characterized in that the total sum of the width of said groove in the section normal to the axis of said head is in a range of $(1/50$ to $2/5) \times \pi D$, except for the endmost terminating portion of the head of the shank, wherein D is the diameter of the section normal to the axis of said head of said shank.

As mentioned above, since the groove comes into continuously alternate contact with the hard abrasive grains-attached section, and the total sum of the width of the groove, not attached with hard abrasive grains, in the section normal to the axis of said head is in a range of $(1/50$ to $2/5) \times \pi D$, except for the endmost terminating portion of the head of the shank, wherein D has the same meaning as mentioned above, satisfactory cutting efficiency is assured in the respective sections, while satisfactory removal of debris and heat is achieved. In addition, since it is very unlikely that the portion of teeth or dental restorations to be cut by using said cutting tool may be machined in the form of a groove, it is not required to readjust that portion with an ordinary grooveless cutting tool.

BRIEF DESCRIPTION OF THE DRAWINGS

The aforesaid and other objects and features of the present invention will become apparent from the following detailed description with reference to the accompanying drawings, which are given for the purpose of illustration alone, and in which:

FIG. 3 is a side view of a second embodiment of the cutting tool according to the present invention, FIG. 4 is an enlarged end view taken along the line IV—IV of FIG. 3, FIG. 5 is a side view of a third embodiment of the cutting tool according to the present invention, and FIG. 6 is an enlarged end view taken along the line VI—VI of FIG. 5.

DETAILED DESCRIPTION OF THE PREFERRED EMBODIMENTS OF THE INVENTION

Figure 1:
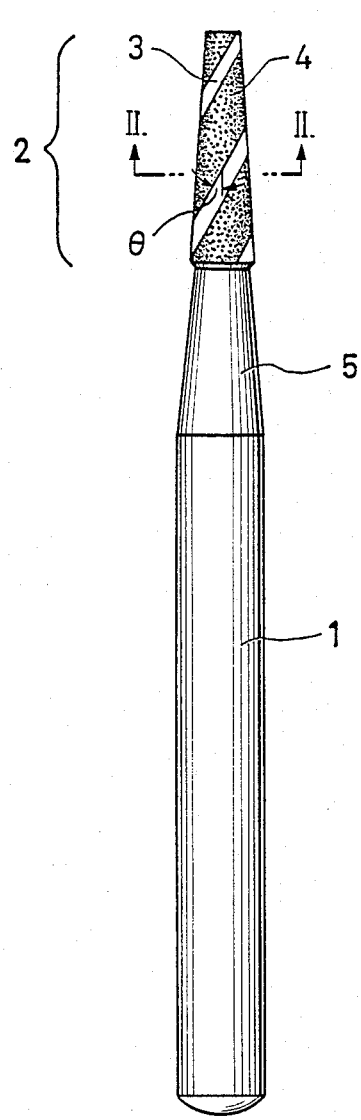
FIG. 1 is a side view of a first embodiment of the cutting tool according to the present invention.

A shank 1 is formed of a steel wire of good machinability, which has a strength resisting to high-speed cutting. A stainless steel wire of good corrosion resistance is preferred to this end. The shank 1 includes a 2 which is basically of a conical, cylindrical or spherical shape. It is noted that the head 2 may be of a combination of such shapes. The head 2 of the shank 1 is provided on its outer face portion with one or two or more dextrally spiral grooves 3 which may be of various cross-sectional shapes including semicircular, V-type and U-type shapes, if cutting efficiency and effective removal of debris and heat are assured. Hard abrasive grains 4 are also fixedly provided on its outer face portion, except for the groove(s) 3. The hard abrasive grains 4 may be formed of natural or artificial diamond, aluminum oxide, carborundum, cubic boron nitride, TiC ceramics, $ZrO_2$ ceramics, $Si_3N_4$ ceramics and the like. Generally, the attachment of hard abrasive grains may be achieved by making use of nickel or chromium electroplating as illustrated in the first embodiment of FIGS. 1 and 2 as well as in the third embodiment of FIGS. 5 and 6. Alternatively, use may be made of brazing as illustrated in the second embodiment of FIGS. 3 and 4, which may be applied alone or in combination with electroplating. A neck 5 is provided between the head 2 and the shank 1.

There are some ways to manufacture the present invention.

First way is the best, that is: each spiral groove 3 is mechanically formed prior to the attachment of the hard abrasive grains 4 to the head 2 of the shank 1. After each groove 3 has been insulated, hard abrasive grains are attached on to the outer face portion of the head 2 except for each groove 3 by electroplating. Second way is as follows: a dextrally spiral insulation may be formed on the outer face portion of the head 2 of the shank 1 prior to the attachment of the hard abrasive grains 4 thereto, and the hard abrasive grains 4 may then be attached to the outer surface portion, except for the insulation, by means of electroplating. Third way is as follows: it may also be possible to attach the hard abrasive grains 4 to the head 2 of the shank 1 by electroplating or brazing and, thereafter, applying dextrally the spiral machined to the outer face portion of the head 2 to form each groove 3. Basically, each groove 3 should preferably be of the same width w in its entire length; however, the present invention is not exclusively limited to such an arrangement. For instance, when the head 2 of the shank 1 is of a conical shape, it is required to decrease gradully the width w of each groove 3 toward its endmost portion, since to form it on that endmost portion is difficult in view of processing and gives rise to a lowering of cutting efficiency. This is also effective for removing debris. When the head of the shank is of a spherical shape, on the other hand, it is preferred to decrease gradually the width w of the or each groove 3, since the peripheral speed of the head is so decreased in the vicinity of its endmost portion that little or no cutting efficiency is obtained in that portion.

Referring to the width w of the or each groove 3 freed of any abrasive grain attachment, the total sum W of the width w of the or each groove 3 in the section normal to the axis of the head 2 of the shank 1 should be in a range of $(1/50$ to $2/5) \times \pi D$ that is equal to or less than ½ of the length of the outer circumference of the cross-section of the head 2 of the shank 1 except for its endmost terminating portion, wherein D is the outer diameter of the section perpendicular to the axis of the head 2 of the shank 1. When the total sum W of the width w of the or each groove 3 is less than $(1/50) \times \pi D$, the continuously alternate contact of the or each groove 3 with the abrasive grains-attached portion does not produce its own effect, thus resulting in a lowering of cutting efficiency and difficulty being involved in the removal of debris and heat. When the total sum W of the width w of the or each groove 3 exceeds $(2/5) \times \pi D$, the area ratio of the abrasive grains-attached portion 4 in the head 2 of the shank 1 is so reduced that the removal of debris and heat is easily effected, but there is a drop in cutting efficiency.

An angle $\theta$ of inclination with respect to the axis of the head 2 of the shank 1 is a particular factor having an influence upon cutting efficiency. Particularly excellent cutting efficiency is obtained when the angle $\theta$ is just or at about 0°. Since large impacts are then applied upon teeth or dental restorations therefor, however, a patient tends to suffer pain. This tendency decreases as the angle $\theta$ of inclination increases from 0° to up to 5°. However, if the angle $\theta$ of inclination is in a range of 5° to 60°, excellent cutting efficiency is assured, while the impacts to be applied upon teeth or dental restorations therefor are reduced in magnitude. An angle $\theta$ of inclination exceeding 60° however, results in a lowering of cutting efficiency. It is therefore preferred that the angle $\theta$ of inclination with respect to the longitudinal axis of the shank 1 is in the range of 5° to 60°. It is understood that the angle $\theta$ of inclination should preferably remain constant along the overall length of the head 2. However, if the length of the neck 5 cannot be increased due to a long length of the head 2, as is the case with the embodiment of FIG. 5, with the result that where it is likely that each dextrally spiral groove 3 extends to the shank 1 in mechanically forming it on the outer face portion of the head 2 of the shank 1, the angle $\theta$ of inclination may be increased in the range of up to 60° only on the shank side of the head 2.

The number of the grooves 3, not filled with hard abrasive grains, is also a factor having a large influence upon cutting efficiency and the removal of debris and heat. In the case of the cutting tool shown in FIG. 1, two grooves 3 are provided. The provision of three or more grooves 3 makes improvements in the removal of debris and heat. However, where the head 2 of the shank 1 has a short diameter and circumferential length, the area of the abrasive grains-attached portion 4 in the head 2 of the shank 1 is so reduced that its area of contact with teeth or dental restorations therefor is reduced, leading to a lowering of cutting efficiency. This tendency becomes marked especially under the application of a low load. It is therefore desired that the number of the grooves 3 is basically two.

Figure 2:
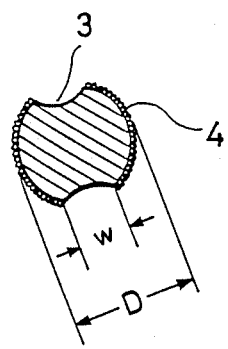
FIG. 2 is an enlarged end view taken along the line II—II of FIG. 1.

In the case of the cutting tool shown in FIG. 3 or 5 wherein the head 2 of the shank 1 is longer than that of the cutting tool of FIG. 1, and is basically of a conical shape, however, it is peferred that the number of the grooves 3 to be formed in the region of the head 2 extending from its central to endmost portions is one. The reasons are that, when two grooves 3 are provided, the outer diameter of the region of the head 2 from its central to endmost portions is so reduced that there is a reduction in the area of the abrasive grains-attached section 4 in the head 2 of the shank 1 and hence the area of contact thereof with a tooth or dental restorations, thus resulting in a lowering in the cutting efficiency of the head 2 from its central to endmost portions.

The dental rotary instrument of the present invention are designed for the purpose of cutting teeth or dental restorations. Thus, no particular limitation is imposed upon the hard abrasive grains applied, if they have the strength required for cutting enamel having a Knoop hardness of around 340 and dental restorations having a Knoop hardness of 30 to 150. It is desired, however, that natural or artificial diamond is used, since it excels particularly in cutting efficiency and durability.

Referring to the cutting tool shown in FIG. 1, the shank 1 includes the head 2 on the outer face portion of which two dextrally spiral grooves 3 are formed in the semi-circular form, each having an angle θ of inclination of 30° with respect to the axis of the shank 1, a width w of 0.35 mm in the section perpendicular to that axis, and a width corresponding to 1/10 to 1/5 of the circumferential length [the total sum W of the width w of the grooves $3=(1/5$ to $2/5)\times\pi D$] of the head 2, except for its endmost terminating portion. The outer face portion of the head 2, except for the grooves 3, is fixedly attached with natural diamond abrasive grains by electroplating to form the hard abrasive grains-attached section 4.

Referring to the cutting tool shown in FIG. 3, the shank 1 is provided on the outer face portion of the head 2 with two dextrally spiral grooves 3 of a V-type shape in cross-section, each having an angle θ of inclination of 10° with respect to the axis of the shank 1, a width w of 0.25 mm in the section normal to that axis, and a width of 3/50 to 7/50 of the circumferential length of the head 2, except for its endmost terminating portion [the total sum W of the width w of the grooves $3=(6/50$ to $14/50)\times\pi D$]. One of the grooves 3 extends from the middle to endmost portions of the head 2, while the two grooves 3 extend from the middle to the shank side on the head 2. The outer face portion of the head 2, except for the grooves 3, is fixedly attached with artificial diamond abrasive grains by brazing to form the hard abrasive grains-attached section 4.

Referring to the cutting tool shown in FIG. 5, the shank 1 is provided on the outer face portion of the head 2 with two dextrally spiral grooves 3, each having angles of inclination of 30° in its region from the endmost portion to a portion 1 mm away from the neck 5 and 50° in the region therefrom to the neck 5 with respect to the axis of the shank 1, a width w of 0.45 mm in the section normal to that axis, and a width of 4/50 to 9/50 of the circumferential length of the head 2, except for its endmost terminating portion [the total sum W of the width w of the grooves $3=(8/50$ to $18/50)\times\pi D$]. One of the grooves 3 extends from the endmost to the vicinity of the endmost portions of the head 2, while the two grooves 3 extend from the vicinity of the endmost portion to the shank side on the head 2. The outer face portion of the head 2, except for the grooves 3, is fixedly attached with artificial diamond abrasive grains by electroplating to form the hard abrasive grains-attached section 4.

The dental rotary instruments as described above and claimed later are mounted to a dental turbine or a dental engine to form a preparation.

Thus, the dental rotary instrument of the present invention includes the shank 1 having the head 2 with the groove or grooves 3 which is or are formed on the outer face portion of the head 2 in the dextrally spiral form alone, and the hard abrasive grains-attached section 4 formed on the outer face portion of the head 2, except for the groove or grooves 3, and, owing to its spiral structure, its cutting workability in operation more similar to that of a dental bur rather than that of a grindstone. In the case of a dental turbine which does not allow the cutting tool to be adjusted in respect of its rotational direction, therefore, the spiral direction of the cutting tool is dextral as is the same with the conventional dental bur. (Particularly, a carbide bur is extremely important for dentists familiar with the conventional procedures.) With the dental rotary instrument of the present invention, there is no fear that teeth or dental restorations may be cut too deeply to impair the tooth because of a difference in the spiral direction. Nor is it necessary for dentists to learn different procedures. Thus, the dental rotary instrument of the present invention can be used in the same manner as heretofore applied.

The dental rotary instrument of the present invention prevents a lowering of cutting efficiency that is one of the disadvantages of the prior art cutting tools described in the preamble of the disclosure. Especially when the dental rotary instrument having the head of a reduced outer diameter is used even under a low load, its cutting efficiency does not drop significantly. Under a high load, its cutting efficiency is further increased. With the invented dental rotary instrument, there is no possibility that teeth or dental restorations may be machined in the form of a groove, when cutting it. Nor is it necessary to re-adjust the cut surface with a usual grooveless dental rotary instrument, since the cut surface is well-finished.

The removal of debris and heat is automatically effected due to the continuous alternate contact of the or each groove with the hard abrasive grains-attached section and the selection of the total sum of the width of the or each groove, which is determined to prevent a lowering of cutting efficiency in spite of such continuous alternate contact. In addition, impacts to be applied upon teeth or dental restorations are adjusted to lower level so that patients do not suffer any pain.

It is thus understood that the dental rotary instrument according to the present invention makes a great deal of contribution to dentistry.

What is claimed is:
1. A dental rotary cutting tool comprising:
   (a) a shank;
   (b) a head; and
   (c) a neck connecting said shank and said head, wherein:
   (d) said head comprises a truncated cone having a surface symmetrical about an axis of revolution;
   (e) at least two dextrally spiral grooves are formed in the surface of said head;
   (f) hard abrasive grains are mounted on the surface of said head except in said at least two dextrally spiral grooves;
   (g) the total sum of the width of said at least two dextrally spiral grooves in all sections normal to the axis of said head except for the endmost terminating portion of said head is in the range of (1/50 to 2/5) times $\pi D$, wherein D is the diameter of the section normal to the axis of said head;
   (h) each of said at least two dextrally spiral grooves has an angle θ of inclination with respect to the axis of said head of 5 degrees to 60 degrees;
   (i) at least one of said at least two dextrally spiral grooves extends at least substantially the entire length of said head; and
   (j) at least one of said at least two dextrally spiral grooves extends from the wider end of said head to a point substantially short of the narrower end of said head.

* * * * *